United States Patent [19]

Harada et al.

[11] Patent Number: 5,717,124

[45] Date of Patent: Feb. 10, 1998

[54] PROCESS FOR PREPARATION OF OXYGLUTARIC ACID ESTER DERIVATIVES

[75] Inventors: Katsumasa Harada; Akio Matsushita; Hiroshi Sasaki; Yasuhiro Kawachi, all of Yamaguchi, Japan

[73] Assignee: Ube Industries, Ltd., Yamaguchi, Japan

[21] Appl. No.: 539,173

[22] Filed: Oct. 4, 1995

Related U.S. Application Data

[63] Continuation-in-part of Ser. No. 218,635, Mar. 28, 1994, abandoned.

[30] Foreign Application Priority Data

Mar. 30, 1993 [JP] Japan ......................... 5-71970
Nov. 19, 1993 [JP] Japan ......................... 5-290863

[51] Int. Cl.$^6$ ......................................... C07F 7/08
[52] U.S. Cl. ................. 556/437; 556/404; 558/87; 560/174
[58] Field of Search .................. 556/404, 437; 558/87; 560/174

[56] References Cited

U.S. PATENT DOCUMENTS

| | | | |
|---|---|---|---|
| 4,686,298 | 8/1987 | Karanewsky et al. | 556/404 X |
| 4,804,770 | 2/1989 | Karanewsky | 556/405 |
| 5,177,239 | 1/1993 | Singh et al. | 556/404 X |

FOREIGN PATENT DOCUMENTS 554455  8/1991  European Pat. Off. .

OTHER PUBLICATIONS

Heathcock et al., *J. Chem. Med.*, 1987, Total Synthesis and Biological Evaluation of Structural Analogues of Compactin and Dihydromevinolin, pp. 1858–1873.

*Primary Examiner*—Paul F. Shaver
*Attorney, Agent, or Firm*—McAulay Fisher Nissen Goldberg & Kiel, LLP

[57] ABSTRACT

A process for preparing an oxyglutaric acid ester derivative of the formula:

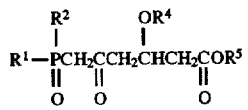

in which each of $R^1$ and $R^2$ is $C_{1-5}$ alkoxy, $C_{1-7}$ aralkyloxy, $C_{7-9}$ halogenated aralkyloxy or phenyl, $R^4$ is a hydroxyl-protecting group, and $R^5$ is $C_{1-10}$ alkyl which may have a substituent, comprises the steps of reacting a methyl phosphonate derivative or methyl phosphine oxide derivative with an oxyglutaric acid mono-ester to give a reaction product which comprises an oxyglutaric acid derivative having a phosphorus-containing group and a pentenedioic acid mono-ester (by-product), removing the pendenedioic acid mono-ester from the reaction product to isolate the oxyglutaric acid derivative, and converting the isolated oxyglutaric acid derivative into the oxyglutaric acid ester derivative. A process for obtaining an optically active oxyglutaric acid ester derivative is also disclosed.

4 Claims, No Drawings

PROCESS FOR PREPARATION OF OXYGLUTARIC ACID ESTER DERIVATIVES

This application is a continuation-in-part of Ser. No. 08/218,635, filed Mar. 28, 1994, now abandoned, the contents of which are hereby incorporated by reference

FIELD OF THE INVENTION

The present invention relates to a novel process for the preparation of oxyglutaric acid ester derivatives, and particularly relates to a process for preparing optically active oxyglutaric acid ester derivatives which are useful as intermediates for preparing blood cholesterol reducing agents [e.g., 3-hydroxy-3-methylglutaric Co-A reductase inhibitor].

BACKGROUND OF THE INVENTION

It is known that oxyglutaric acid ester derivatives are useful as intermediates for preparing blood cholesterol reducing agent [e.g., 3-hydroxy-3-methylglutaric Co-A reductase inhibitor]. For example, a process for preparing a blood cholesterol reducing agent (e.g., compactin) from methyl (R)-3-t-butyldimethylsilyloxy-6-dimethoxyphosphinyl-5-oxohexanoate (optically active oxyglutaric acid ester derivative) is described in Journal of Medicinal Chemistry [J. Med. Chem., 30(1987), No.10, pp. 1858–1873].

As a process for preparing the optically active oxyglutaric acid ester derivative, U.S. Pat. No. 4,804,770 discloses the following process: An oxyglutaric acid monoalkyl ester of which hydroxyl group is protected (represented by formula (II) mentioned hereinafter) is reacted with dimethyl methylphosphonate (represented by formula (I) mentioned hereinafter) in the presence of n-butyl lithium at −78° C. to give a reaction product comprising a phosphonated oxyglutaric acid derivative (represented by formula (III) mentioned hereinafter), and the reaction product is then reacted with diazomethane to give a reaction product comprising the desired ketophosphonate (methylester of the phosphonated oxyglutaric acid derivative), i.e., the above-mentioned optically active oxyglutaric acid ester derivative (represented by formula (IV) mentioned hereinafter).

The above process is simple and appears advantageous. However, according to the study conducted by the present inventors, the reaction product finally obtained by the above process comprises the desired optically active oxyglutaric acid ester derivative as well as a large amount of impurities. Further, it has been noted that the desired oxyglutaric acid ester derivative and some impurities are analogous in their chemical structures to each other. Therefore, it is not easy to separate the desired oxyglutaric acid ester derivative from the impurities by industrially applicable methods.

SUMMARY OF THE INVENTION

The present inventors have found that the reaction product comprising the phosphonated oxyglutaric acid derivative (represented by the formula (III)), that is a compound which is then esterified to give the optically active oxyglutaric acid ester derivative (represented by the formula (IV)), can be easily purified by a simple method advantageously utilizable for industrial production. Further study of the inventors has revealed that the desired optically active oxyglutaric acid ester derivative of the formula (IV) can be prepared with a high purity from the purified phosphonated oxyglutaric acid derivative (III).

The present invention resides in a process for the preparation of an oxyglutaric acid ester derivative of the formula (IV):

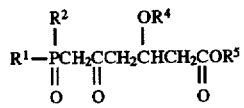

in which each of $R^1$ and $R^2$ independently represents an alkoxy group of 1 to 5 carbon atoms, an aralkyloxy group of 7 to 9 carbon atoms, a halogenated aralkyloxy group of 7 to 9 carbon atoms, or phenyl, $R^4$ represents a hydroxyl-protecting group, and $R^5$ represents an alkyl group of 1 to 10 carbon atoms which may have a substituent, comprising the steps of:

reacting a methyl phosphonate derivative or methyl phosphine oxide derivative of the formula (I):

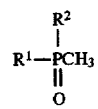

in which $R^1$ and $R^2$ have the meanings as defined above, with an oxyglutaric acid mono-ester of the formula (II):

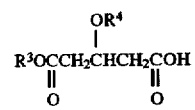

in which $R^3$ represents an alkyl group of 1 to 10 carbon atoms and $R^4$ has the meanings as defined above, to give a reaction product comprising an oxyglutaric acid derivative of the formula (III):

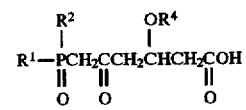

in which $R^1$, $R^2$ and $R^4$ have the meanings as defined above, and a pentenedioic acid mono-ester of the formula (VII):

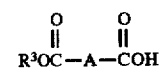

in which $R^3$ has the meaning as defined above, and A represents —CH=CH—CH$_2$— or —CH$_2$—CH=CH—;

removing the pentenedioic acid mono-ester of the formula (VII) from the reaction product to isolate the oxyglutaric acid derivative of the formula (III); and converting the isolated oxyglutaric acid derivative of the formula (III) into the oxyglutaric acid ester derivative of the formula (IV) using an esterifying reagent.

In the above process, the reaction of the methyl phosphonate derivative or methyl phosphine oxide derivative of the formula (I) and the oxyglutaric acid mono-ester of the formula (II) is preferably performed in an organic solvent in the presence of an alkali metal hexamethyldisilazane of the formula (VI):

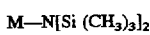

in which M represents an alkali metal.

The step of removing the pentenedioic acid mono-ester of the formula (VII) from the reaction product is preferably performed by washing the reaction product with an aqueous alkaline solution such as an alkali metal salt of a lower aliphatic acid.

In the above process, the esterifying reagent preferably is an alkyl halide of the formula (V):

R⁵X        (V)

in which R⁵ has the meaning as defined in claim 1 and X represents a halogen atom, or a sulfonic acid ester of the formula (V'):

R⁶—S(O₂)—OR⁵        (V')

in which R⁵ has the meaning as defined in claim 1 and R⁶ represents an alkyl group of 1 to 10 carbon atoms or phenyl, which may have a substituent.

The invention also resides in a process for the preparation of an oxyglutaric acid derivative of the formula (III):

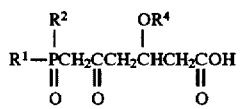        (III)

in which each of $R^1$ and $R^2$ independently represents an alkoxy group of 1 to 5 carbon atoms, an aralkyloxy group of 7 to 9 carbon atoms, a halogenated aralkyloxy group of 7 to 9 carbon atoms, or phenyl, and $R^4$ represents a hydroxyl-protecting group, which comprises:

reacting a methyl phosphonate derivative or methyl phosphine oxide derivative of the formula (I):

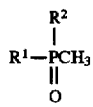        (I)

in which $R^1$ and $R^2$ have the meanings as defined above, with an oxyglutaric acid mono-ester of the formula (II):

(II)

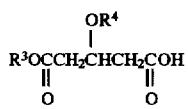        (II)

in which $R^3$ represents an alkyl group of 1 to 10 carbon atoms and $R^4$ has the meanings as defined above, in an organic solvent in the presence of an alkali metal hexamethyldisilazane of the formula (VI):

M—N[Si(CH₃)₃]₂        (VI)

in which M represents an alkali metal.

The invention further resides in a process for the preparation of an oxyglutaric acid ester derivative of the formula (IV):

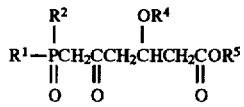        (IV)

in which each of $R^1$ and $R^2$ independently represents an alkoxy group of 1 to 5 carbon atoms, an aralkyloxy group of 7 to 9 carbon atoms, a halogenated aralkyloxy group of 7 to 9 carbon atoms, or phenyl, $R^4$ represents a hydroxyl-protecting group, and $R^5$ represents an alkyl group of 1 to 10 carbon atoms which may have a substituent, which comprises:

reacting an oxyglutaric acid derivative of the formula (III):

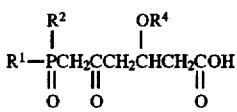        (III)

in which $R^1$, $R^2$ and $R^4$ have the meanings as defined above, with an esterifying reagent which is selected from the group consisting of an alkyl halide of the formula (V):

R⁵X        (V)

in which R⁵ has the meaning as defined in claim 1 and X represents a halogen atom, and a sulfonic acid ester of the formula (V'):

R⁶—S(O₂)—OR⁵        (V')

in which R⁵ has the meaning as defined in claim 1 and R⁶ represents an alkyl group of 1 to 10 carbon atoms or phenyl, which may have a substituent.

The invention further resides in a process for the preparation of a (R)-oxyglutaric acid ester derivative of the formula (IV):

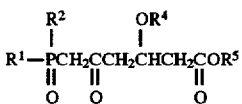        (IV)

in which each of $R^1$ and $R^2$ independently represents an alkoxy group of 1 to 5 carbon atoms, an aralkyloxy group of 7 to 9 carbon atoms, a halogenated aralkyloxy group of 7 to 9 carbon atoms, or phenyl, $R^4$ represents a hydroxyl-protecting group, and $R^5$ represents an alkyl group of 1 to 10 carbon atoms which may have a substituent, comprising the steps of:

optically resolving a racemate of an oxyglutaric acid mono-ester of the formula (II):

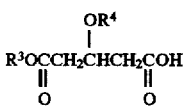        (II)

in which $R^3$ represents an alkyl group of 1 to 10 carbon atoms and $R^4$ has the meanings as defined above to give a (S)-oxyglutaric acid mono-ester of the formula (II), reacting a methyl phosphonate derivative or methyl phosphine oxide derivative of the formula (I):

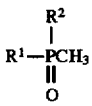        (I)

in which $R^1$ and $R^2$ have the meanings as defined above, with the (S)-oxyglutaric acid mono-ester of the formula (II) to give a (R)-oxyglutaric acid derivative of the formula (III):

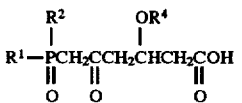        (III)

in which $R^1$, $R^2$ and $R^4$ have the meanings as defined above, and converting the isolated (R)-oxyglutaric acid derivative of the formula (III) into the (R)-oxyglutaric acid ester derivative of the formula (IV) using an esterifying reagent.

The invention furthrmore resides in process for optically resolving a racemate of an oxyglutaric acid mono-ester of the formula (II):

$$R^3OCCH_2CHCH_2COH \quad (II)$$
with $OR^4$ on middle C, and C=O groups (O double bonded)

in which $R^3$ represents an alkyl group of 1 to 10 carbon atoms and $R^4$ is t-butyldimethylsilyl group to recover a (S)-3-t-butyldimethylsilyloxyglutaric acid monoalkyl ester using (S)-(-)-α-methyl-p-nitrobenzylamine.

In the invention, the reaction product comprising the phosphonated oxyglutaric acid derivative of the formula (III) and the by-product (i.e., a pentenedioic acid mono-ester of the formula (VII)) is treated to isolate the desired phosphonated oxyglutaric acid derivative form the by-product, and then the isolated phosphonated oxyglutaric acid derivative is converted into the oxyglutaric acid ester derivative of the formula (IV) using an esterifying reagent. Thus obtained oxyglutaric acid ester derivative is almost free from contamination with the by-product which cannot be easily removed by industrially applicable methods.

DETAILED DESCRIPTION OF THE INVENTION

The oxyglutaric acid ester derivative of the formula (IV) is basically prepared by the following three steps.

Step 1):

A step of reacting a methyl phosphonate derivative or methyl phosphine oxide derivative of the formula (I) with an oxyglutaric acid mono-ester of the formula (II) to give a reaction product comprising an oxyglutaric acid derivative of the formula (III) (e.g., phosphonated oxyglutaric acid derivative) and, which is illustrated as follows:

$$R^1-PCH_3 + R^3OCCH_2CHCH_2COH \longrightarrow$$
(I) with $R^2$ and O; (II) with $OR^4$ and O groups -continued $$R^1-PCH_2CCH_2CHCH_2COH$$
with $R^2$, $OR^4$ substituents (III)

Step 2):
A step of purifying the reaction product to separate the oxyglutaric acid derivative of the formula (III) from a by-product.

Step 3):
A step of converting the purified oxyglutaric acid derivative of the formula (III) into the oxyglutaric acid ester derivative of the formula (IV) using an esterifying reagent such as an alkyl halide ($R^5X$) or a sulfonic acid ester ($R^6-S(O_2)-OR^5$), which is illustrated as follows:

$$R^1-PCH_2CCH_2CHCH_2COH + R^5X \longrightarrow$$
with $R^2$, $OR^4$ (III)

$$R^1-PCH_2CCH_2CHCH_2COR^5$$
with $R^2$, $OR^4$ (IV)

The steps 1) to 3) are explained hereinafter in more detail.

The step 1) can be carried out, for instance, in the following manner.

Before the reaction of the methyl phosphonate derivative or methyl phosphine oxide derivative (wherein $R^1$ and $R^2$ of the formula (I) both are phenyl) of the formula (I) and the oxyglutaric acid mono-ester of the formula (II) is performed, the methyl phosphonate derivative or methyl phosphine oxide derivative of the formula (I) (hereinafter referred to as phosphorus-containing compound) and an alkali metal hexamethyldisilazane (e.g., lithium bistrimethylsilylamide) of the formula (VI):

$$M-N[Si(CH_3)_3]_2 \quad (VI)$$

in which M represents an alkali metal;

are caused to react with each other in an organic solvent to form an alkali metal salt of the phosphorus-containing compound, which is illustrated as follows:

$$R^1-PCH_3 + M-N[Si(CH_3)_3]_2 \xrightarrow{\text{Organic solvent (I)}} R^1-P-CH_2M + HN[Si(CH_3)_3]_2$$
with $R^2$; Solution (A+B)

Subsequently, the resultant alkali metal salt is reacted with the oxyglutaric acid mono-ester of the formula (II) to give the oxyglutaric acid derivative of the formula (III), which is illustrated as follows:

$$R^3OCCH_2CHCH_2COH + \text{Solution (A + B)} \longrightarrow$$
with $OR^4$ $$R^1-PCH_2CCH_2CHCH_2COH$$
with $R^2$, $OR^4$ The first step is performed, for example, in the following manner.

In the first step, the phosphorus-containing compound such as methylphosphonate derivative can be used with no solvent. However, the phosphorus-containing compound is generally used in the form of a solution prepared by dissolving it in an organic solvent (hereinafter referred to as Solution A).

The alkali metal hexamethyldisilazane is used in the form of a solution prepared by dissolving it in an organic solvent (hereinafter referred to as Solution B).

Solution A and Solution B are brought into contact with each other for causing a reaction to give a solution containing an alkali metal salt of the phosphorus-containing compound (Solution (A+B)). In this process, Solution A is dropwise added with stirring to Solution B which is beforehand chilled to a temperature of −50° C. to 0° C. (preferably a temperature of −30° C. to 0° C.) to give Solution (A+B). Otherwise, Solution B can be dropwise added to Solution A. The reaction period preferably is in the range of 10–120 minutes, and more preferably in the range of 30–60 minutes.

The alkali metal salt of the phosphorus-containing compound is well stable in an organic solvent. Therefore, the salt is generally prepared by reacting the phosphorus-containing compound with the alkali metal hexamethyldisilazane in an organic solvent.

In the formula (I) representing the phosphorus-containing compound (methylphosphonate derivative or methyl phosphine oxide derivative), examples of the alkoxy group having 1–5 carbon atoms represented by $R^1$ and $R^2$ include methoxy, ethoxy, n-propoxy, isopropoxy, butoxy, and pentyloxy; examples of the aralkyloxy group having 7–9 carbon atoms include benzyloxy and phenethyloxy (preferably benzyloxy); and examples of the halogenoaralkyloxy group having 7–9 carbon atoms include halogenophenylmethoxy, halogenophenylethyloxy and halogenophenylpropyloxy (preferably halogenophenylmethyloxy). The alkoxy group is preferred for $R^1$ and $R^2$. Particularly preferred are methoxy and ethoxy, and methoxy is most preferred. Accordingly, the phosphorus-containing compound preferably is the methylphosphonate derivative.

If the phosphorus-containing compound is in the form of liquid at room temperature, it can be used with no solvent, but also can be used in the form of a solution in an organic solvent. This solution can be prepared by dissolving the compound in an organic solvent. Any organic solvents can be used, provided that they do not participate in the reaction. Examples of the employable organic solvents include aliphatic hydrocarbons such as hexane and heptane; ethers such as tetrahydrofuran (THF) and isopropyl ether; and aromatic hydrocarbons such as benzene and toluene. Preferred are hexane, benzene and THF. The phosphorus-containing compound can be dissolved in the solvent to give a solution having a concentration of not less than 1% (wt/vol %), preferably not less than 5%, and more preferably not less than 10%.

In the formula (VI) representing the alkali metal hexamethyldisilazane, examples of the alkali metal represented by M include lithium, sodium and potassium. Lithium and sodium are preferred, and lithium is most preferred. The alkali metal hexamethyldisilazane can be used in the form of a solution in an organic solvent. Any organic solvents can be used, provided that they do not participate in the reaction. Examples of employable solvents include hexane, THF and ethylbenzene. Hexane and THF are preferred. These solvents can be used in combination in any proportions. The alkali metal hexamethyldisilazane can be dissolved in an organic solvent to give a solution having a concentration of 1–50% (wt/vol %), preferably 5–45%, more preferably 10–40%, and most preferably 10–30%. The ratio between the phosphorus-containing compound and the alkali metal hexamethyldisilazane generally is in the range of 1:0.1–1:1.1 (molar ratio), preferably 1:0.4–1:1.1, more preferably 1:0.5–1:1, and most preferably 1:0.7–1:1.

Organic solvent (I) set forth in the above-illustrated reaction formula is an organic solvent for dissolving the alkali metal hexamethyldisilazane to prepare the organic solution, or a mixture of organic solvents for dissolving the phosphorus-containing compound to prepare the organic solution.

The second step is performed, for instance, in the following manner.

The oxyglutaric acid mono-ester represented by the formula (II) can be used with no solvent, or in the form of an organic solution prepared by dissolving it in an organic solvent.

The aforementioned Solution (A+B) is kept at a temperature of −50° C. to 0° C. and is brought into contact with the oxyglutaric acid mono-ester of the formula (II) to cause a reaction for preparing a solution containing an alkali metal salt of the oxyglutaric acid mono-ester. In this reaction, for example, the solution of the oxyglutaric acid mono-ester is dropwise added with stirring to Solution (A+B) kept at a temperature of −50° C. to 0° C., so as to cause a reaction. Otherwise, Solution (A+B) can be dropwise added to the solution of the oxyglutaric acid mono-ester. At the end of the reaction period, a reaction terminator such as a saturated aqueous solution of ammonium chloride can be added. The reaction period preferably is in the range of 10–600 minutes, and more preferably in 30–300 minutes. The reaction temperature preferably is in the range of −50° C.–0° C., and more preferably in the range of −30° C.—0° C.

In the formula (II) representing the oxyglutaric acid mono-ester, examples of the alkyl group of 1–10 carbon atoms represented by $R^3$ include methyl, ethyl, propyl and its isomer (i.e., isopropyl), butyl and its isomers, pentyl and its isomers, hexyl and its isomers, heptyl and its isomers, octyl and its isomers, nonyl and its isomers, and decyl and its isomers, and the alkyl group preferably is methyl, ethyl, n-propyl or isopropyl. Examples of an alkyl group having substituent groups include an alkyl group substituted with one or more aryl (e.g., 1-phenylethyl and 1-naphtylethyl), and an alkyl group substituted with one or more aryl and one or more carboxyl such as α-phenyl-α-benzylcarbonylmethyl and α-phenyl-α-benzyloxycarbonylmethyl. Preferred examples of an alkyl group represented by $R^3$ are those having 1–6 carbon atoms, particularly methyl, ethyl, n-propyl and isopropyl.

Examples of a hydroxyl-protecting group represented by $R^4$ include ether-forming groups such as methyl, ethyl, propyl, butyl, t-butyl, allyl, benzyl, tetrahydropyranyl, t-butyldimethylsilyl and t-butylphenylsilyl; ester-forming groups such as acetyl and benzoyl; and sulfonic acid-forming groups such as methylsulfonyl, p-toluenesulfonyl and phenylsulfonyl. The ether-forming groups are preferred, and t-butyldimethylsilyl is most preferred.

If the oxyglutaric acid mono-ester of the formula (II) is in the form of liquid at room temperature, it can be used with no solvent. The mono-ester can be also used in the form of a solution prepared by dissolving the mono-ester in an organic solvent which does not participate in the reaction.

The ratio between the phosphorus-containing compound of the formula (I) and the oxyglutaric acid mono-ester of the formula (II) generally is in the range of 1:0.05–1:0.33 (molar ratio), preferably 1:0.1–1:0.3, and more preferably 1:0.15–1:0.25.

Examples of the solvents include aliphatic hydrocarbons such as hexane and heptane; ethers such as tetrahydrofuran (THF) and isopropyl ether; and aromatic hydrocarbons such as benzene and toluene. Preferred are hexane, toluene and THF. The oxyglutaric acid mono-ester is dissolved in such solvents and is generally used as a solution having a concentration of 1–60% (wt/vol %), preferably 5–50%, and more preferably 10–40%.

Otherwise, the oxyglutaric acid mono-ester can be prepared in the manner described in Japanese Patent Provisional Publications No. 2(1990)-256650 and No. 5(1993)-32680.

Alternatively, Step 1) can be performed in the following manner:

The phosphorus-containing compound (methyl phosphonate derivative or methyl phosphine oxide derivative) of the formula (I) is reacted with a base or basic material (e.g., n-butyl lithium, or lithium isopropylamide) in tetrahydrofuran (THF) or the like to give a salt of the phosphorus-containing compound, whereby a tetrahydrofuran solution or suspension containing the salt of the phosphorus-containing compound is obtained. Then, a solution of the oxyglutaric acid mono-ester of the formula (II) in an inert solvent is dropwise added with stirring to the tetrahydrofuran solution or suspension containing the salt, to prepare a salt of the oxyglutaric acid derivative, and a mineral acid (e.g., HCl) is added to the solution of the salt to give the oxyglutaric acid derivative of the formula (III).

The reaction is generally conducted at a temperature of $-110°$ C.$-40°$ C., and preferably $-110°$ C.$-50°$ C. The ratio between the base and the phosphorus-containing compound generally is in the range of 0.8–1.2 (base/phosphorus-containing compound, molar ratio), and preferably 0.9–1.1. The ratio between the phosphorus-containing compound and the oxyglutaric acid mono-ester generally is in the range of 2–8 (phosphorus-containing compound/oxyglutaric acid mono-ester, molar ratio), preferably 2.5–8, more preferably 3–7.

In the formula (III) representing the oxyglutaric acid derivative prepared in Step 1), $R^1$, $R^2$ and $R^4$ have the same meaning as defined above. The groups of $R^1$, $R^2$ and $R^4$ of the oxyglutaric acid derivative are determined depending upon the above-mentioned phosphorus compound and oxyglutaric acid mono-ester. Preferred examples of the oxyglutaric acid derivative of the formula (III) include 3-t-butyldimethylsilyloxy-6-dialkoxyphosphinyl-5-oxohexanoic acid (which has an alkoxy group wherein the alkyl group has 1–3 carbon atoms). Most preferred is 3-t-butyldimethylsilyloxy-6-dimethoxyphosphinyl-5-oxohexanoic acid.

In this step, the oxyglutaric acid mono-ester of the formula (II) preferably is an optically active compound having a configuration of (S), that is, (S)-oxyglutaric acid mono-ester. The optically active compound can be obtained from a racemate of the oxyglutaric acid mono-ester using an optically resolving reagent. Preferred examples of the resolving reagent include (S)-(-)-α-methyl-p-nitrobenzylamine, (S)-(-)-phenethylamine, (S)-(-)-1-naphthylethylamine, (S)-(-)-2-aminobutanol, (S)-(-)-2-aminopropanol, and (S)-(-)-cyclohexylethylamine. (S)-(-)-α-methyl-p-nitrobenzylamine is most preferred. When the optically active (S)-oxyglutaric acid mono-ester is used, the resulting oxyglutaric acid derivative of the formula (III) is an optically active compound having the configuration represented by R, that is, (R)-oxyglutaric acid derivative.

The optical resolution of the oxyglutaric acid mono-ester of the formula (II) can be performed in the following manner. The racemete (i.e., a racemic mixture) of 3-t-butyldimethylsilyloxyglutaric acid mono-ester and (S)-(-)-α-methyl-p-nitrobenzylamine are dissolved in a solvent and the solvent is removed in vacuo. Thus, (S)-(-)-α-methyl-p-nitrobenzylamine salt of (S)-3-t-butyldimethylsilyloxyglutaric acid mono-ester [salt A] and (S)-(-)-α-methyl-p-nitrobenzylamine salt of (R)-3-t-butyldimethylsilyloxyglutaric acid mono-ester [salt B] are formed. Subsequently, a salt which is the same as salt A is added as a seed crystal to a solution of the salt A and the salt B in a solvent end then is cooled to precipitate the salt A. The resultant salt A is then separated to give (S)-3-t-butyldimethylsilyloxyglutaric acid mono-alkyl ester and (S)-(-)-α-methyl-p-nitrobenzylamine salt. Thus, the (S)-3-t-butyldimethylsilyloxyglutaric acid mono-alkyl ester is isolated. The separation is performed, for example, by the steps of adding the salt A to an organic solvent immiscible with water to form a suspension, adding a dilute hydrochloric acid to the suspension to give a mixture of the mono-alkyl ester and the amine salt, and recovering the mono-alkyl ester with the organic solvent from the mixture. Thus, (S)-3-t-butyldimethylsilyloxyglutaric acid mono-alkyl ester is obtained.

Otherwise, the racemate of 3-t-butyldimethylsilyloxyglutaric acid mono-ester and (S)-(-)-α-methyl-p-nitrobenzylamine is dissolved in a solvent under heating and the solution is then cooled to room temperature to precipitate the salt A, more preferentially than the salt B. Thereafter, the separation is performed in the same manner as above.

The resultant oxyglutaric acid derivative of the formula (III) can be isolated in Step 2) in the following manner.

The oxyglutaric acid derivative of the formula (III) is first obtained from the solution containing the alkali metal salt of the oxyglutaric acid derivative. A mineral acid such as dilute hydrochloric acid is added to the solution to make the solution acidic, and then an organic solvent is added to the acidic solution to extract the oxyglutaric acid derivative. The extract is then dried and concentrated in vacuo to obtain the oxyglutaric acid derivative.

Preferred examples of the mineral acid include hydrochloric acid and sulfuric acid, and hydrochloric acid is most preferred. Examples of the solvents used for the extraction include esters such as ethyl acetate, alkyl halides such as methylene chloride and chloroform, ethers such as diethyl ether and diisopropyl ether and aromatic hydrocarbons such as benzene, toluene and xylene. Preferred are ethyl acetate, methylene chloride, isopropyl ether, and toluene.

The oxyglutaric acid derivative of the formula (III) is then purified, for instance, by washing the oxygluraric acid derivative with an aqueous alkaline solution. This washing procedure is described below in more detail.

The reaction product of Step 1) generally contains the oxyglutaric acid derivative of the formula (III) as well as a pentenedioic acid mono-ester of the formula (VII):

in which $R^3$ and A have the meaning as defined hereinbefore, which is a main by-product produced in the reaction between the phosphorus-containing compound (methyl phosphonate derivative or methyl phosphine oxide derivative) of the formula (I) and the oxyglutaric acid mono-ester of the formula (II).

The oxyglutaric acid derivative obtained above is dissolved in an organic solvent, and to the resulting solution is added an aqueous alkaline solution. After stirring or shaking, an organic portion is separated from the aqueous portion, and processed to remove the solvent so as to isolate the desired oxyglutaric acid derivative of the formula (III).

According to the study of the present inventors, the by-product in the reaction between the methyl phosphonate derivative or methyl phosphine oxide derivative of the formula (I) and the oxyglutaric acid mono-ester of the formula (II), particularly the pentenedioic acid mono-ester of the formula (VII), is well soluble in an aqueous alkaline solution, as compared with the desired oxygluraric acid derivative of thed formula (III). Therefore, the desired purification of the oxyglutaric acid derivative of the formula (III) is easily performed by washing a solution of the reaction product (the oxyglutaric acid derivative) in an organic solvent with an aqueous alkaline solution. In the process, the by-product is easily transferred into the aqueous portion, and therefore separated from the desired oxyglutaric acid derivative.

Examples of alkaline materials to prepare the aqueous alkaline solution include alkali metal hydroxides, alkali metal carbonates, alkali metal hydrogencarbonates, and alkali metal salts of organic acids. Examples of the hydroxides, carbonates and hydrogen carbonates of alkali metal are lithium hydroxide, lithium carbonate, sodium hydroxide, sodium carbonate, sodium hydrogencarbonate, potassium hydroxide, potassium carbonate, and potassium hydrogencarbonate. Examples of the alkali metal salts of organic acids include alkali metal salts (e.g., sodium salt, potassium salt, and lithium salt) of lower aliphatic acids having 1–6 carbon atoms. Preferred are alkali metal salts of acetic acid, propionic acid, isopropionic acid, and butyric acid. Particularly preferred are sodium acetate and potassium acetate. The alkali metal salt of the aliphatic acid or other organic acid can be prepared in the aqueous solution to be used for the washing.

Examples of the organic solvents used for the above extraction and purification process include esters of lower alcohols (having 1–6 carbon atoms) and lower carboxyric acid (having 1–6 carbon atoms) such as methyl acetate and ethyl acetate, alkyl halides such as methylene chloride and chloroform, ethers such as diethyl ether and diisopropyl ether, and aromatic hydrocarbons such as benzene, toluene and xylene. Ethyl acetate, methylene chloride and toluene are preferably employed.

The purification using an aqueous alkaline solution which contains a salt of an alkali metal and a lower aliphatic acid can be performed, for example, as follows.

The lower aliphatic acid is reacted with an aqueous solution of the alkali metal salt to prepare an aqueous solution containing the alkali metal salt of the aliphatic acid, and then the resulting solution is added to the solution of the reaction product (or the obtained oxyglutaric acid derivative of the formula (III)) in an organic solvent.

The molar ratio between the lower aliphatic acid and the alkali metal (of the alkali metal salt) is in the range of 1:0.2–1:1.1, and preferably 1:0.2–1:1.0 based on 1 mole of the lower aliphatic acid.

The amount of the lower aliphatic acid to be dissolved in water (i.e., molar concentration) is not particularly restricted, provided that it can be dissolved. Generally, the molar concentration is in the range of 0.1–5 mole/l, preferably 0.2–4 mole/l.

The alkali metal salt of the lower aliphatic acid can be formed, for example, by dissolving the lower aliphatic acid and the alkali metal salt in water with stirring the above-described ratio. The formed alkali salt of the lower aliphatic acid can be used in the form of the aqueous solution without isolation.

The alkali metal salt of the lower aliphatic acid may be isolated, purified and dried, and then the dried alkali metal salt may be stored in the solid form. Such stored alkali metal salt of a lower aliphatic acid can be also dissolved in water for the use in the purification process. In this case, the amount of alkali salt of lower aliphatic acid to be dissolved in water (i.e., molar concentration) can be the same as described above. The aqueous alkaline solution thus prepared can be dealt in the same manner as the above-described aqueous alkaline solution from which the alkali metal salt of a lower aliphatic acid is not isolated.

The molar ratio between the total of the oxyglutaric acid derivative of the formula (III) and the pentenedioic acid mono-ester of the formula (VII), and the alkali metal salt of a lower aliphatic acid usually is in the range of 1:0.2–1:10 [(oxyglutaric acid derivative+pentenedioic acid mono-ester)/alkali metal salt], preferably 1:0.3–1:8. The concentrations of the oxyglutaric acid derivative and the pentenedioic acid mono-ester in the organic solvent and that of the alkali salt of a lower aliphatic acid in the aqueous alkaline solution are not restricted.

The amount of the alkali metal salt to be dissolved in water (i.e., molar concentration) is not particularly restricted providing that it can be dissolved. Generally, the molar concentration is in the range of 0.1–5 mole/l, preferably 0.2–4 mole/l.

The organic portion separated from the aqueous portion can be dried over a drying reagent such as anhydrous magnesium sulfate or anhydrous sodium sulfate, and then the dried organic portion can be placed under reduced pressure to distill off the solvent, so as to obtain the purified oxyglutaric acid derivative of the formula (III). From thus obtained oxyglutaric acid derivative or directly from the obtained organic solution containing the oxyglutaric acid derivative, the desired optically active oxyglutaric acid ester derivative of the formula (IV) such as methyl (R)-3-t-butyldimethylsilyloxy-6-dimethoxyphosphinyl-5-oxohexanoate can be obtained.

The step 3) is explained below in more detail.

The oxyglutaric acid derivative of the formula (III), a base and the alkyl halide of the formula (V; $R^5X$) as an esterifying reagent are dispersed in an organic solvent (Organic solvent (II)) to cause reaction, whereby the oxyglutaric acid derivative is converted into the oxyglutaric acid ester derivative of the formula (IV):

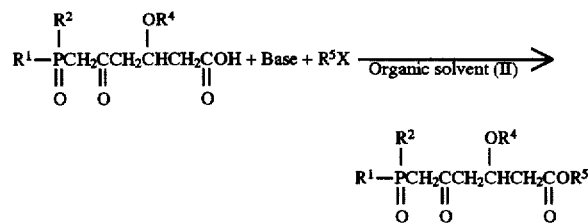

The reaction period generally is in the range of 1–24 hrs., preferably 2–16 hrs., and more preferably 3–12 hrs. The reaction temperature generally is in the range of 0°–60° C., preferably 10°–50° C. and more preferably 15°–40° C.

Organic solvent (II) used in Step 3) is an organic solvent in which the oxyglutaric acid derivative, the base and the alkyl halide are dissolved or dispersed. Any organic solvents can be used, provided that they do not participate in the reaction. Examples of Organic solvent (II) include lower alcohols such as methanol and ethanol, ketones such as acetone and methyl ethyl ketone, esters such as methyl acetate and ethyl acetate, alkyl halides such as methylene chloride and chloroform, aromatic hydrocarbons such as benzene, toluene and xylene, and non-protonic polar liquid compounds such as dimethylformamide (DMF), dimethyl sulfoxide (DMSO), acetonitrile, and hexamethylphosphoroamide(HMPA). Acetone, methylene chloride, acetonitrile, ethyl acetate and DMF are preferred, and acetone, methylene chloride and acetonitrile are particularly preferred. Although the amount of Organic solvent (II) is not restricted, the amount preferably is in the range of 0.5–20 liters, more preferably 0.6–10 liters, based on 1 mole of the oxyglutaric acid derivative.

In the formula (V) representing the alkyl halide used in Step 3), $R^5$ represents an alkyl group having 1–10 carbon atoms which may have a substituent. Examples of the alkyl group include methyl, ethyl, propyl and its isomer, butyl and its isomers, pentyl and its isomers, hexyl and its isomers, heptyl and its isomers, octyl and its isomers, nonyl and its isomers and decyl and its isomers, the isomers of each group containing no tertiary isomer. Preferred is an alkyl group having 1–6 carbon atoms. Paticularly preferred is methyl. Examples of the substituent include phenyl which may have a substituent. Examples of the substituent which may be attated to the phenyl include nitro, halogen (e.g., fluorine, bromine, chlorine, or iodo), alkyl of 1–4 carbon atoms (e.g., methyl, ethyl, propyl, isopropyl, butyl or isobutyl), alkoxy of 1–4 carbon atoms (e.g., methoxy, ethoxy, propoxy, isopropoxy, or butoxy). Nitro, chlorine, and methyl are preferred, and methyl is most preferred. Examples of a halogen atom represented by X in the formula (V) include chlorine atom, bromine atom and iodine atom. Preferred are bromine atom and iodine atom. The ratio between the oxyglutaric acid derivative and the alkyl halide generally is in the range of 1:0.8–1:10 (molar ratio), preferably 1:0.9–1:9.0, and more preferably 1:1.0–1:7.0.

Examples of the alkyl halide of the formula (V) include methyl chloride, methyl bromide, methyl iodide, ethyl chloride, ethyl bromide, ethyl iodide, 4-chlorobenzyl bromide, α-bromo-p-xylene, 4-nitrobenzyl bromide, 4-nitrobenzyliodide, and benzyl bromide. Preferred are methyl bromide, methyl iodide, 4-chlorobenzyl bromide, α-bromo-p-xylene, 4-nitrobenzyl bromide and benzyl bromide. The most preferred are methyl iodide and benzyl bromide.

The esterifying reagent may be a sulfonic acid ester of the formula (V'):

$$R^6-S(O_2)-OR^5 \qquad (V')$$

in which $R^5$ has the meaning as defined above, and $R^6$ represents an alkyl group of 1 to 10 carbon atoms or phenyl, which may have a substituent.

Examples of alkyl group for $R^6$ include methyl, ethyl, propyl, isopropyl, butyl, isobutyl, tert-butyl, pentyl, hexyl, heptyl, octyl, nonyl and decyl. Preferred is alkyl of 1–4 carbon atoms, and methyl is most preferred. The substituent preferably is phenyl which may have a substituent. Examples of the substituent which may be attated to the phenyl include nitro, halogen (e.g., fluorine, bromine, chlorine, or iodo), alkyl of 1–4 carbon atoms (e.g., methyl, ethyl, propyl, isopropyl, butyl or isobutyl), alkoxy of 1–4 carbon atoms (e.g., methoxy, ethoxy, propoxy, isopropoxy, or butoxy). Nitro, chlorine, and methyl are preferred, and methyl is most preferred. Preferred for $R^6$ are methyl and p-tolyl.

Examples of the sulfonic acid ester of the formula (V') include the following:

methyl methanesulfonate, ethyl methanesulfonate, propyl methanesulfonate, isopropyl methanesulfonate, butyl methanesulfonate, pentyl methanesulfonate, hexyl methanesulfonate, heptyl methanesulfonate, octyl methanesulfonate, nonyl methanesulfonate, and decyl methanesulfonate;

methyl ethanesulfonate, ethyl ethanesulfonate, propyl ethanesulfonate, isopropyl ethanesulfonate, butyl ethanesulfonate, pentyl ethanesulfonate, hexyl ethanesulfonate, heptyl ethanesulfonate, octyl ethanesulfonate, nonyl ethanesulfonate, and decyl ethanesulfonate;

methyl propanesulfonate, ethyl propanesulfonate, propyl propanesulfonate, isopropyl propanesulfonate, butyl propanesulfonate, pentyl propanesulfonate, hexyl propanesulfonate, heptyl propanesulfonate, octyl propanesulfonate, nonyl propanesulfonate, and decyl propanesulfonate;

methyl isopropanesulfonate, ethyl isopropanesulfonate, propyl isopropanesulfonate, isopropyl isopropanesulfonate, butyl isopropanesulfonate, pentyl isopropanesulfonate, hexyl isopropanesulfonate, heptyl isopropanesulfonate, octyl isopropanesulfonate, nonyl isopropanesulfonate, and decyl isopropanesulfonate;

methyl butanesulfonate, ethyl butanesulfonate, propyl butanesulfonate, isopropyl butanesulfonate, butyl butanesulfonate, pentyl butanesulfonate, hexyl butanesulfonate, heptyl butanesulfonate, octyl nonyl butanesulfonate, and decyl butanesulfonat;

methyl p-toluenesulfonate, ethyl p-toluenesulfonate, propyl p-toluenesulfonate, isopropyl p-toluenesulfonate, butyl p-toluenesulfonate, pentyl p-toluenesulfonate, hexyl p-toluenesulfonate, heptyl p-toluenesulfonate, octyl p-toluenesulfonate, nonyl p-toluenesulfonate, and decyl p-toluenesulfonate;

methyl benzenesulfonate, ethyl benzenesulfonate, propyl benzenesulfonate, isopropyl benzenesulfonate, butyl benzenesulfonate, pentyl benzenesulfonate, hexyl benzenesulfonate, heptyl benzenesulfonate, octyl benzenesulfonate, nonyl benzenesulfonate, and decyl benzenesulfonate;

methyl nitrobenzenesulfonate, ethyl nitrobenzenesulfonate, propyl nitrobenzenesulfonate, isopropyl nitrobenzenesulfonate, butyl nitrobenzenesulfonate, pentyl nitrobenzenesulfonate, hexyl nitrobenzenesulfonate, heptyl nitrobenzenesulfonate, octyl nitrobenzenesulfonate, nonyl nitrobenzenesulfonate, and decyl nirtobenzenesulfonate;

methyl chlorobenzenesulfonate, ethyl chlorobenzenesulfonate, propyl chlorobenzenesulfonate, isopropyl chlorobenzenesulfonate, butyl chlorobenzenesulfonate, pentyl chlorobenzenesulfonate, hexyl chlorobenzenesulfonate, heptyl chlorobenzenesulfonate, octyl chlorobenzenesulfonate, nonyl chlorobenzenesulfonate, and decyl chlorobenzenesulfonate;

methyl methoxoybenzenesulfonate, ethyl methoxybenzenesulfonate, propyl methoxybenzenesulfonate, isopropyl methoxybenzenesulfonate, butyl methoxybenzenesulfonate, pentyl methoxybenzenesulfonate, hexyl methoxybenzenesulfonate, heptyl methoxybenzenesulfonate, octyl methoxybenzenesulfonate, nonyl methoxybenzenesulfonate, and decyl methoxybenzenesulfonate.

Preferred are methyl α-toluenesulfonate and methyl methanesulfonate.

The ratio between the oxyglutaric acid derivative and the sulfonic acid ester generally is in the range of 1:0.8–1:10 (molar ratio), preferably 1:0.9–1:9.0, and more preferably 1:1.0–1:7.0.

Examples of the base used in Step 3) include alkali metal carbonates and alkali metal hydrogencarbonates. Preferred examples of the base include sodium carbonate, sodium hydrogencarbonate, potassium carbonate and potassium hydrogencarbonates. Potassium carbonate and potassium hydrogencarbonates are particularly preferred. The ratio between the oxyglutaric acid derivative and the base generally is in the range of 1:0.8–1:2.5 (molar ratio), preferably 1:0.9–1:2.0, and more preferably 1:1–1:1.5.

In the formula (IV) representing the oxyglutaric acid ester derivative, each of $R^1$, $R^2$, $R^4$ and $R^5$ has the same meaning as defined above. The oxyglutaric acid ester derivative having such $R^1$, $R^2$, $R^4$ and $R^5$ is determined depending upon the above-mentioned glutaric acid mono-ester and alkyl halide. Preferred examples of the oxyglutaric acid ester derivative include alkyl 3-t-butyldimethylsilyloxyglutarate (which has an alkyl group having 1–6 carbon atoms). Most preferred is methyl 3-t-butyldimethylsilyloxy-6-dimethoxyphosphinyl-5-oxohexanoate.

After the resultant oxyglutaric acid ester derivative is extracted with the solvent and concentrated under reduced pressure, if desired, the derivative can be further purified.

Each of the oxyglutaric acid mono-ester, the oxyglutaric acid derivative and the oxyglutaric acid ester derivative has an asymmetric carbon atom. Therefore, they can be in the form of any optical isomers. In the invention, they preferably are optically active compounds.

In the invention, optical purity of the oxyglutaric acid mono-ester is essentially the same as that of the obtained optical active oxyglutaric acid ester derivative. In other words, the optical purity does not change during the oxyglutaric acid mono-ester and the obtained optical active oxyglutaric acid ester derivative.

The present invention is further illustrated by the following examples, but those examples are given by no means to restrict the invention. The optical purity of each example was measured by means of HPLC under the following conditions.

1) The conditions for measurement of the optical purity of monomethyl 3-t-butyldimethylsilyloxyglutarate Column: CHIRALCEL OD (4.6 mm ID×250 mmL)

Eluent: Mixture of hexane, ethanol and trifluoroacetic acid (hexane: ethanol: trifluoroacetic acid=95:5:0.01)

Flow rate: 0.5 ml/minute

Detected by: UV (wavelength: 220 nm)

Temperature: Room temperature (25° C.)

Concentration: 10 mg/1 ml (1 ml: eluent)

2) The conditions for measurement of optical purity of methyl 3-t-butyldimethylsilyloxy-6-dimethoxyphosphinyl-5-oxohexanoate Column: CHIRALPAK AD (4.6 mm ID×250 mmL)

Eluent: Mixed solvent of hexane and isopropanol (hexane: isopropanol=9:1)

Flow rate: 0.5 ml/minute

Detected by: UV (wavelength: 285 nm)

Temperature: Room temperature (25° C.)

Concentration: 10 mg/1 ml (1 ml: eluent)

EXAMPLE 1

Preparation of monomethyl (S)-3-t-butyldimethylsilyloxyglutarate

The above compound was obtained by optically resolving monomethyl 3-t-butyldimethylsilyloxyglutarate (racemate) in the following manner.

In 55.6 ml of a mixture of hexane and toluene (hexane: toluene=2:1) was dissolved 10.40 g of monomethyl 3-t-butyldimethylsilyloxyglutarate to prepare a solution. The resultant solution was heated with stirring to 67° C. 6.30 g of (S)-(-)-α-methyl-p-nitrobenzylamine was dropwise added to the solution, the solution being kept at 65°–70° C. After the dropwise addition was complete, the solution was cooled to 20° C. after 2 hours and filtered to collect a crystalline product. The crystalline product was washed with 14.6 ml of a mixture of hexane and toluene (hexane:toluene= 2:1) and then washed with 14.6 ml of hexane. The washed crystalline product was dried to obtain 7.75 g of a white crystalline product (A).

To the white crystalline product (A) were added 14.6 ml of toluene, and the crystalline product (A) was dissolved in the toluene by heating 70° C. to prepare a solution. 25.7 ml of hexane was dropwise added with stirring to the solution to precipitate a crystalline product, the solution being kept at 65°–70° C. The solution was stirred at 65°–70° C. for 1 hour, and then was cooled to 20° C. for 2 hours, and the precipitate was filtered to collect a crystalline product. The crystalline product was washed with 15.5 ml of a mixture of hexane and toluene (hexane:toluene=2:1) and then washed with 15.5 ml of hexane, whereby 7.08 g of a white crystalline product (B) was obtained. The yield was 85% based on the amount of monomethyl (S)-3-t-butyldimethylsilyloxyglutarate.

To the white crystalline product (B) were added 42.2 ml of toluene and 13.4 ml of water, and a resultant mixture was stirred to prepare a suspension. 2N Hydrochloric acid was added to the suspension until the aqueous layer showed pH 2. The added amount of 2N hydrochloric acid was approx. 8.64 ml. The suspension was stirred at room temperature for 1 hour, and then was separated into the organic portion and the aqueous portion. The organic portion was washed with 4.8 ml of water and was dried over anhydrous magnesium sulfate. The organic portion was subjected to filteration and concentrated in vacuo to give 4.42 g of mono-methyl (S)-3-t-butyldimethylsilyloxyglutarate (yield: 100%; optical purity: 98% ee).

All the aqueous portions were combined, and 6.0 ml of aqueous 4N-sodium hydroxide solution was added to the combined aqueous portion. The aqueus portion was stirred, and then was extracted with three portions of dichloromethane (1 portion of 8.4 ml and 2 portions of 4.2 ml). The extracts were combined and dried over anhydrous magnesium sulfate, and then subjected to filtration and concentrated in vacuo to give 2.64 g of (S)-(-)-α-methyl-p-nitrobenzylamine (yield: 99%).

Preparation of (R)-3-t-butyldimethylsilyloxy-6-dimethoxyphosphinyl-5-oxohexanoic acid In an atmosphere of argon, 2.71 g of methyl dimethylphosphonate was dissolved with stirring in 6.1 ml of tetrahydrofuran (THF) to prepare a solution. The solution was chilled to –10° C., and then 19.7 ml of THF solution of 1M lithium hexamethyldisilazane was dropwise added to the solution with stirring at the temperature. After the dropwise addition was complete, the solution was further stirred for 1 hour at the temperature (–10° C.). To the resulting solution, THF solution containing 1.21 g of mono-methyl (S)-3-t-butyldimethylsilyloxyglutarate (optical purity: 98% ee) which was obtained above was dropwise added, and then the solution was further stirred for 3 hours at the temperature. 8.1 ml of saturated aqueous solution of ammonium chloride was dropwise added to the resultant solution to terminate the reaction. After the obtained solution was allowed to stand at room temperature, 44 ml of 1N hydrochloric acid was dropwise added to the solution, and then the solution was extracted with two portions of 15 ml of ethyl acetate. The ethyl acetate portions were combined and were dried over anhydrous magnesium sulfate. The solvent was removed by distillation in vacuo to give a concentrated solution. The concentrated solution was placed on a silica gel column and eluted with a mixture of hexane, ethyl acetate and acetic acid (hexane:ethyl acetate:acetic acid=7:3:1) to obtain 1.05 g of (R)-3-t-butyldimethylsilyloxy-6-dimethoxyphosphinyl-5-oxohexanoic acid as an oil (yield: 65% based on the amount of the glutaric acid mono-ester).

The analytical values of the obtained compound were in good agreement with the values shown in J. Org. Chem., 57(1992), 1935.

Preparation of methyl (R)-3-t-butyldimethylsilyloxy-6-dimethoxyphosphinyl-5-oxohexanoate 1.05 g of (R)-3-t-butyldimethylsilyloxy-6-dimethoxyphosphinyl-5-oxohexanoic acid prepared above was dissolved in 16 ml of acetone to prepare the solution. To the solution, 2.02 g of methyl iodide and 0.391 g of potassium carbonate were added with stirring, and then the solution was further stirred for 5 hours at room temperature. After 16 ml of water was added to the solution, the solution was extracted with two portions of 20 ml of ethyl acetate. The ethyl acetate portions were combined and dried over anhydrous magnesium sulfate, and then the solvent was removed by distillation in vacuo to give 1.0 g of methyl (R)-3-t-butyldimethylsilyloxy- 6-dimethoxyphosphinyl-5-oxohexanoate as an oil (optical purity: 98% ee; yield: 92% based on the amount of (R)-3-t-butyldimethylsilyloxy-6-dimethoxyphosphinyl-5-oxohexanoic acid).

The analytical values of the obtained compound was in good agreement with the values shown in J. Org. Chem., 56(1991), 3744].

EXAMPLE 2

Preparation of (R)-3-t-butyldimethylsilyloxy-6-dimethoxyphosphinyl-5-oxohexanoic acid In an atmosphere of argon, 5.44 g of methyl dimethylphosphonate was dropwise added with stirring to 40 ml of THF solution of 1M lithium hexamethyldisilazane at $-10°$ C. The solution was further stirred for 1 hour at that temperature. To the resultant solution, 40 ml of THF solution containing 2.42 g of monomethyl (S)-3-t-butyldimethylsilyloxyglutarate (optical purity: 98% ee) which had been prepared in the same manner as Example 1 was dropwise added, and then the solution was further stirred for 3 hours at that temperature. 16.1 ml of saturated aqueous solution of ammonium chloride was dropwise added to the solution to terminate the reaction. The obtained solution was allowed to stand at room temperature, and 88 ml of 1N hydrochloric acid was dropwise added to the solution and then the solution was extracted with two portions of 30 ml of ethyl acetate. The ethyl acetate portions were combined and dried over anhydrous magnesium sulfate. The solvent of the solution was removed by distillation in vacuo to obtain a concentrated solution. The concentrated solution was placed on a silica gel column and eluted with a mixture of hexane, ethyl acetate and acetic acid (hexane:ethyl acetate:acetic acid=7:3:1)] to give 2.61 g of (R)-3-t-butyldimethylsilyloxy-6-dimethoxyphosphinyl-5-oxohexanoic acid as an oil (yield: 82% based on the amount of the half ester of glutaric acid derivative).

The analytical values of the obtained compound were in good agreement with the values shown in J. Org. Chem., 57(1992), 1935.

Thereafter, procedures were performed in the same manner as those in Example 1 to obtain 2.46 g of methyl (R)-3-t-butyldimethylsilyloxy-6-dimethoxyphosphinyl-5-oxohexanoate as an oil (optical purity: 98% ee; Yield: 91% based on the amount of (R)-3-t-butyldimethylsilyloxy-6-dimethoxyphosphinyl-5-oxohexanoic acid).

The analytical values of the obtained compound were in good agreement with the values shown in J. Org. Chem., 56(1991), 3744].

EXAMPLE 3

Preparation of (R)-3-t-butyldimethylsilyloxy-6-dimphenylphosphinoyl-5-oxohexanoic acid In an atmosphere of argon, 14.3 g of methyl dimethylphosphine oxide was dissolved in 80 ml of THF and chileed to $-78°$ C. to prepare a solution of methyl dimethylphosphine oxide. To the solution was added 38 ml of a hexane solution containing 1.6M butyl lithium, and the mixture was stirred for 1 hour at the temperature. To the resultant solution, 40 ml of THF solution containing 5 g of mono-methyl (S)-3-t-butyldimethylsilyloxyglutarate (optical purity: 98% ee) which had been obtained in the same manner as Example 1 was dropwise added, and then the solution was further stirred for 2 hours at the temperature. 38 ml of saturated aqueous ammonium chloride solution was added to the solution. The obtained solution was allowed to stand and its temperature was increased to room temperature. 65 ml of 1N hydrochloric acid was dropwise added to the solution, and then the solution was extracted with 200 ml of ethyl acetate. The ethyl acetate portion was shaken with a mixture of hydrochloric acid and saturated sodium chloride solution, and then dried over anhydrous magnesium sulfate. The solvent was removed by distillation in vacuo to give a concentrated solution. The concentrated solution was placed on a silica gel column and eluted with a mixture of hexane, ethyl acetate, and acetic acid (7:3:1)] to give 6.2 g of (R)-3-t-butyldimethylsilyloxy-6-diphenylphosphinoyl-5-oxohexanoic acid as an glass substance (yield: 71% based on the amount of the glutaric acid mono-ester).

$[\alpha]_D^{25.0}-11.7°$ (c=1.05; methanol)

$^1$H-NMR(CDCl$_3$) δ:

0.02 (s, 3H), 0.06 (s, 3H), 0.80 (s, 9H), 2.51 (d, 2H, J=6.4 Hz), 2.98 (d, 1H, J=6.8 Hz), 2.99 (d, 1H, J=5.4 Hz), 3.57–3.88 (m, 2H), 4.49–4.55 (m, 1H), 7.48–7.62 (m, 6H), 7.70–7.83 (m, 4H).

IR-spectra (liquid film) 1719, 1715, 1438, 1170, 1120 (cm$^{-1}$)

Preparation of methyl (R)-3-t-butyldimethylsilyloxy-6-diphenylphosphinoyl-5-oxohexanoate To 0.92 g (2 mmol.) of (R)-3-t-butyldimethylsilyloxy-6-diphenylphosphinoyl-5-oxohexanoic acid prepared above, 0.28 g of methyl iodide, 0.28 g of potassium carbonate and 10 ml of acetone were added, and then the mixture was stirred for 8 hours at room temperature. After 16 ml of water was added to the solution, the solution was extracted with two portions of 20 ml of ethyl acetate. The ethyl acetate portions were combined and dried over anhydrous magnesium sulfate, and then the solvent was removed by distillation in vacuo to give 0.81 g of methyl (R)-3-t-butyldimethylsilyloxy-6-diphenylphosphinoyl-5-oxohexanoate as a colorless oil (optical purity: 98% ee; yield: 85% based on the amount of (R)-3-t-butyldimethylsilyloxy-6-diphenylphosphinoyl-5-oxohexanoic acid).

$[\alpha]_D^{25.0}$ −14.1° (c=1.06; methanol)

$^1$H-NMR (CDCl$_3$) δ:

0.01 (s, 3H), 0.03 (s, 3H), 0.09 (s, 9H), 2.42 (d, 1H, J=6.8 Hz), δ-2.43 (d, 1H, J=5.4 Hz), 2.93 (d, 2H, J=5.9 Hz), 3.63 (d, 2H, J=15.1 Hz), 3.64 (s, 3H), 4.45–4.55 (m, 1H), 7.44–7.57 (m, 4H), 7.71–7.82 (m, 4H).

IR-spectra (liquid film) 1739, 1711, 1438, 1198, 1120 (cm$^{-1}$)

CIMS (m/z)

475 (M$^+$+1), 475 (M$^+$-t-Bu), 343 (M$^+$-OSiMe$_2$-t-Bu).

EXAMPLE 4

Preparation of (R)-3-t-butyldimethylsilyloxy-6-dimethoxyphosphinyl-5-oxohexanoic acid In an atmosphere of argon, 78.6 ml of THF solution of 1M lithium hexamethyldisilazane was dropwise added to 9.75 g of methyl dimethylphosphonate at −10° C. The resultant mixture was stirred for 1 hour at the temperature. To the solution, a solution of 4.65 g of monomethyl (S)-3-t-butyldimethylsilyloxyglutarate (optical purity: 98% ee), which was obtained in the same manner as Example 1, in 78.6 ml of hexane was dropwise added with stirring, and then the mixed solution was further stirred for 1 hour at −10° C. To the resultant solution, 19 ml of saturated aqueous ammonium chloride solution was dropwise added to terminate the reaction. After 108 ml of 1.5N hydrochloric acid was dropwise added to the obtained solution, 60 ml of ethyl acetate was added to the solution, and the solution was extracted with ethyl acetate. The ethyl acetate portions were combined and dried over anhydrous sodium sulfate. After filtration, the solvent was removed by distillation in vacuo to give the concentrate. Then, 40.7 ml of ethyl acetate was added to the concentrate to prepare a solution of the concentrate. To the prepared solution, an aqueous solution of 1.81 g of sodium carbonate in 40.7 ml of water was added and then the extraction was carried out. The aqueous portions were combined and made acidic with 1.5N hydrochloric acid. Then, 59.7 ml of ethyl acetate was added to the aqueous portion and the extraction was carried out again. The organic portions were combined. The ratio between (R)-3-t-butyldimethylsilyloxy-6-dimethoxyphosphinyl-5-oxohexanoic acid and pentenedioic acid mono-ester contained in the solution was measured by means of HPLC and found to be 5:1 (molar ratio).

To the above solution, an aqueous solution containing 2.56 g of acetic acid and 1.70 g of sodium hydroxide in 9.7 ml of water was added, and then the extraction was carried out. The organic portion was collected and dried over anhydrous sodium sulfate. After filtration, the solvent was removed by distillation in vacuo to give 4.71 g of (R)-3-t-butyldimethylsilyloxy-6-dimethoxyphosphinyl-5-oxohexanoic acid. The ratio between (R)-3-t-butyldimethylsilyloxy-6-dimethoxyphosphinyl-5-oxohexanoic acid and pentenedioic acid was measured by means of HPLC and found to be 99:1 or less (molar ratio), yield: 75%.

The analytical values of $^1$H-NMR of the obtained (R)-3-t-butyldimethylsilyloxy-6-dimethoxyphosphinyl-5-oxohexanoic acid were in good agreement with the values shown in J. Org. Chem., 57(1992), 1935.

Preparation of methyl (R)-3-t-butyldimethylsilyloxy-6-dimethoxyphosphinyl-5-oxohexanoate Using 4.71 g of the (R)-3-t-butyldimethylsilyloxy-6-dimethoxyphosphinyl-5-oxohexanoic acid prepared above, the procedures were performed in the same manner as those in Example 1 to obtain 4.45 g of methyl (R)-3-t-butyldimethylsilyloxy-6-dimethoxyphosphinyl-5-oxohexanoate as an oil (optical purity: 98% ee; yield: 91% based on the amount of (R)-3-t-butyldimethylsilyloxy-6-dimethoxyphosphinyl-5-oxohexanoic acid).

The analytical values of the obtained compound were in good agreement with the values shown in J. Org. Chem., 56(1991), 3744].

The (R)-3-t-butyldimethylsilyloxy-6-dimethoxyphosphinyl-5-oxohexanoic acid and pentenedioic acid mono-ester which were formed in Examples 4–6 were esterified with diazomethane to give their methyl esters in the ordinary manner, and then the ratio between them was measured by means of HPLC under the following conditions.

The conditions of HPLC measurement

Column: Unisil Q CN, 4.6 mmφ250 mm

Eluent: Mixture of hexane and ethanol (hexane:ethanol= 90:10)

Flow rate: 0.5 ml/minute

Detector: UV spectrophotometer

Wavelength: 220 nm

Temperature: 25° C.

Pressure: 10 kg/cm$^2$

Retention time: methyl ester of (R)-3-t-butyldimethylsilyloxy-6-dimethoxyphosphinyl-5-oxohexanoic acid: 14.121 min. dimethyl ester of pentenedioic acid: 8.878 min.

EXAMPLE 5

Preparation of (R)-3-t-butyldimethylsilyloxy-6-dimethoxyphosphinyl-5-oxohexanoic acid A solution containing (R)-3-t-butyldimethylsilyloxy-6-dimethoxyphosphinyl-5-oxohexanoic acid and pentenedioic acid mono-ester was obtained in the same manner as in Example 4. The ratio of the acid and mono-ester was measured by means of HPLC and found to be 5:1 (molar ratio).

To the above solution, 2.56 g of acetic acid and an aqueous solution of 3.75 g of sodium hydrogencarbonate in 50 ml of water were added, and then the extraction was carried out. The organic portion was collected and dried over anhydrous sodium sulfate. After filtration, the solvent was removed by distillation in vacuo to give 4.65 g of (R)-3-t-butyldimethylsilyloxy-6-dimethoxyphosphinyl-5-oxohexanoic acid. The ratio between (R)-3-t-butyldimethylsilyloxy-6-dimethoxyphosphinyl-5-oxohexanoic acid and pentenedioic acid mono-ester was measured by means of HPLC and found to be 99:1 or less (molar ratio), yield: 75%.

The analytical values of $^1$H-NMR of the obtained (R)-3-t-butyldimethylsilyloxy-6-dimethoxyphosphinyl-5-oxohexanoic acid were in good agreement with the values shown in J. Org. Chem., 57(1992), 1935.

Preparation of methyl (R)-3-t-butyldimethylsilyloxy-6-dimethoxyphosphinyl-5-oxohexanoate Using 4.65 g of the (R)-3-t-butyldimethylsilyloxy-6-dimethoxyphosphinyl-5-oxohexanoic acid prepared above, the procedures were performed in the same manner as those in Example 1 to give 4.39 g of methyl (R)-3-t-butyldimethylsilyloxy-6-dimethoxyphosphinyl-5-oxohexanoate as an oil (optical purity: 98% ee; yield: 91% based on the amount of (R)-3-t-butyldimethylsilyloxy-6-dimethoxyphosphinyl-5-oxohexanoic acid).

EXAMPLE 6

Preparation of (R)-3-t-butyldimethylsilyloxy-6-dimethoxyphosphinyl-5-oxohexanoic acid A solution containing (R)-3-t-butyldimethylsilyloxy-6-dimethoxyphosphinyl-5-oxohexanoic acid and pentenedioic acid mono-ester was obtained in the same manner as in Example 4. The ratio of the acid and mono-ester was measured by means of HPLC and found to be 5:1 (molar ratio).

To solution, an aqueous solution of 3.5 g of sodium acetate in 10 ml of water was added, and the extraction was carried out. The organic portion was collected and dried over anhydrous magnesium sulfate. After filtration, the solvent was removed by distillation in vacuo to give 4.68 g of (R)-3-t-butyldimethylsilyloxy-6-dimethoxyphosphinyl-5-oxohexanoic acid. The ratio between (R)-3-t-butyldimethylsilyloxy-6-dimethoxyphosphinyl-5-oxohexanoic acid and pentenedioic acid mono-ester was measured by means of HPLC and found to be 99:1 or less (molar ratio), yield: 75%. The analytical values of $^1$H-NMR of the obtained (R)-3-t-butyldimethylsilyloxy-6-dimethoxyphosphinyl-5-oxohexanoic acid were in good agreement with the values shown in J. Org. Chem., 57(1992), 1935.

Preparation of methyl (R)-3-t-butyldimethylsilyloxy-6-dimethoxyphosphinyl-5-oxohexanoate Using 4.68 g of the (R)-3-t-butyldimethylsilyloxy-6-dimethoxyphosphinyl-5-oxohexanoic acid prepared above, the procedures were performed in the same manner as those in Example 1 to give 4.42 g of methyl (R)-3-t-butyldimethylsilyloxy-6-dimethoxyphosphinyl-5-oxohexanoate as an oil (optical purity: 98% ee; yield: 91% based on the amount of (R)-3-t-butyldimethylsilyloxy-6-dimethoxyphosphinyl-5-oxohexanoic acid).

EXAMPLE 7

Preparation of methyl (R)-3-t-butyldimethylsilyloxy-6-dimethoxyphosphinyl-5-oxohexanoate 2.58 g (7.0 mmol.) of (R)-3-t-butyldimethylsilyloxy-6-dimethoxyphosphinyl-5-oxohexanoic acid was dissolved in 16 ml of acetone. To the acetone solution were added 6.52 g (35 mmol.) of methyl p-toluenesulfonate and 1.06 g (7.7 mmol.) of potassium carbonate, and the resulting mixture was vigorously stirred for 6 hours at room temperature to give a reaction solution. The reaction solution was mixed with 16 ml of water and then extracted with 20 ml of toluene. The toluene portion was dried over anhydrous magnesium sulfate and concentrated to give an oil. The oil was treated by column chromatography (eluent: ethyl acetate) to give 1.91 g (5.0 mmol.) of methyl (R)-3-t-butyldimethylsilyloxy-6-dimethoxyphosphinyl-5-oxohexanoate as an oil (yield: 71%).

EXAMPLE 8

Preparation of methyl (R)-3-t-butyldimethylsilyloxy-6-dimethoxyphosphinyl-5-oxohexanoate 1.84 g (5.0 mmol.) of (R)-3-t-butyldimethylsilyloxy-6-dimethoxyphosphinyl-5-oxohexanoic acid was dissolved in 11.5 ml of acetone. To the acetone solution were added 0.94 g (5.0 mmol.) of methyl p-toluenesulfonate and 0.76 g (5.5 mmol.) of potassium carbonate, and the resulting mixture was vigorously stirred for 14 hours at room temperature to give a reaction solution. The reaction solution was mixed with 12 ml of water and then extracted with 20 ml of toluene. The toluene portion was dried over anhydrous magnesium sulfate and concentrated to give an oil. The oil was treated by column chromatography (eluent: ethyl acetate) to give 1.41 g (3.7 mmol.) of methyl (R)-3-t-butyldimethylsilyloxy-6-dimethoxyphosphinyl-5-oxohexanoate as an oil (yield: 74%).

EXAMPLE 9

Preparation of methyl (R)-3-t-butyldimethylsilyloxy-6-dimethoxyphosphinyl-5-oxohexanoate 1.84 g (5.0 mmol.) of (R)-3-t-butyldimethylsilyloxy-6-diphenylphosphinyl-5-oxohexanoic acid was dissolved in 11.5 ml of acetone. To the acetone solution were added 0.55 g (5.0 mmol.) of methyl methanesulfonate and 0.76 g (5.5 mmol.) of potassium carbonate, and the resulting mixture was vigorously stirred for 12 hours at room temperature to give a reaction solution. The reaction solution was mixed with 12 ml of water and then extracted with 20 ml of toluene. The toluene portion was dried over anhydrous magnesium sulfate and concentrated to give an oil. The oil was treated by column chromatography (eluent: ethyl acetate) to give 1.45 g (3.8 mmol.) of methyl (R)-3-t-butyldimethylsilyloxy-6-dimethoxyphosphinyl-5-oxohexanoate as an oil (yield: 76%),

EXAMPLE 10

Preparation of benzyl (R)-3-t-butyldimethylsiloxy-6-dimethoxyphosphinyl-5-oxohexanoate 1.84 g (4.99 mmol.) of (R)-3-t-butyldimethylsilyloxy-6-dimethoxyphosphinyl-5-oxohexanoic acid was dissolved in 11.5 ml of acetone. To the acetone solution were added 2.56 g (15.0 mmol.) of benzyl bromide and 0.76 g (5.5 mmol.) of potassium carbonate, and the resulting mixture was vigorously stirred for 6 hours at room temperature to give a reaction solution. The reaction solution was mixed with 12 ml of water and then extracted with 12 ml of toluene. The toluene portion was dried over anhydrous magnesium sulfate and concentrated to give an oil. The oil was treated by column chromatography (eluent: ethyl acetate) to give 1.99 g (4.34 mmol.) of benzyl (R)-3-t-butyldimethylsilyloxy-6-dimethoxyphosphinyl-5-oxohexanoate (optical purity: 99% ee) as an oil (yield: 87%).

$^1$H-NMR(CDCl$_3$) δ:

0.057 (s, 6H), 0.83 (s, 9H), 2.53 (dd, J=6.4 Hz, 15.1 Hz, 1H), 2.59 (dd, J=5.9 Hz, 15.1 Hz, 1), 2.89 (d, J=5.9 Hz, 2H), 3.06 (s, 1H), 3.12 (s, 1H), 3.76 (s, 3H), 3.79 (s, 3H), 4.58 (q, J=5.9 Hz, 1H), 5.08 (d, J=12.5 Hz, 1H), 5.13 (d, J=12.5 Hz, 1H), 7.27–7.37 (m, 5H)

MASS(CI) m/e=459 (M+1), 401 (M-58), 327 (m-132)

COMPARISON EXAMPLE 1

The concentrated solution (1.88 g) containing (R)-3-t-butyldimethylsilyloxy-6-dimethoxyphosphinyl-5-oxohexanoic acid, which was prepared by concentrating the ethyl acetate portion, was obtained in the same manner as Example 1. To the solution, 24 ml of acetone were added to prepare an acetone solution. 3.1 g of methyl iodide and 0.60 g of potassium carbonate were added to the solution with stirring, and then the mixture was further stirred for 5 hours at room temperature. After 24 ml of water was added to the solution, the solution was extracted with two portios of 30 ml of ethyl acetate. The ethyl acetate portions were combined and dried over anhydrous magnesium sulfate. Then, the solvent was removed by distillation in vacuo to give 1.2 g of methyl (R)-3-t-butyldimethylsilyloxy-6-dimethoxyphosphinyl-5-oxohexanoate as an oil (optical purity: 98% ee; purity: 79%).

What we claim is:

1. A process for the preparation of a (R)-oxyglutaric acid ester derivative of the formula (IV):

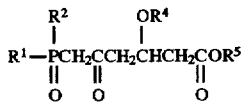   (IV)

in which each of $R^1$ and $R^2$ independently represents an alkoxy group of 1 to 5 carbon atoms, an aralkyloxy group of 7 to 9 carbon atoms, a halogenated aralkyloxy group of 7 to 9 carbon atoms, or phenyl, $R^4$ represents a hydroxyl-protecting group, and $R^5$ represents an alkyl group of 1 to 10 carbon atoms which may have a substituent, comprising the steps of:

optically resolving a racemate of an oxyglutaric acid mono-ester of the formula (II):

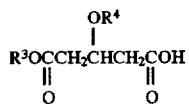   (II)

in which $R^3$ represents an alkyl group of 1 to 10 carbon atoms and $R^4$ has the meanings as defined above to give a (S)-oxyglutaric acid mono-ester of the formula (II), reacting a methyl phosphonate derivative or methyl phosphine oxide derivative of the formula (I):

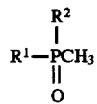   (I)

in which $R^1$ and $R^2$ have the meanings as defined above, with the (S)-oxyglutaric acid mono-ester of the formula (II) to give a (R)-oxyglutaric acid derivative of the formula (III):

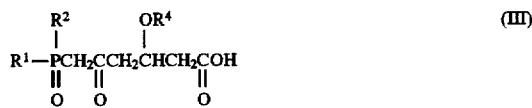   (III)

in which $R^1$, $R^2$ and $R^4$ have the meanings as defined above, and converting the isolated (R)-oxyglutaric acid derivative of the formula (III) into the (R)-oxyglutaric acid ester derivative of the formula (IV) using an esterifying reagent having an $R^5$ group.

2. The process of claim 1, wherein the reaction of the methyl phosphonate derivative or methyl phosphine oxide derivative of the formula (I) and the (S)-oxyglutaric acid mono-ester of the formula (II) is performed in an organic solvent in the presence of an alkali metal hexamethyldisilazane of the formula (VI):

   (VI)

in which M represents an alkali metal.

3. The process of claim 1, wherein the step of optically resolving the racemate of an oxyglutaric acid mono-ester of the formula (II) is performed using (S)-(-)-α-methyl-p-nitrobenzylamine.

4. A process for optically resolving a racemate of an oxyglutaric acid mono-ester of the formula (II):

   (II)

in which $R^3$ represents an alkyl group of 1 to 10 carbon atoms and $R^4$ is t-butyldimethylsilyl group to recover a (S)-3-t-butyldimethylsilyloxyglutaric acid monoalkyl ester using (S)-(-)-α-methyl-p-nitrobenzylamine.

* * * * *